(12) United States Patent
Fan

(10) Patent No.: US 11,160,573 B2
(45) Date of Patent: Nov. 2, 2021

(54) SCANNING URETEROSCOPE FOR MAXIMIZING EFFICIENCY IN LASER LITHOTRIPSY

(71) Applicant: Gyrus ACMI, Inc., Southborough, MA (US)

(72) Inventor: Tailin Fan, Nashua, NH (US)

(73) Assignee: Gyrus Acmi, Inc., Westborough, MA (US)

( * ) Notice: Subject to any disclaimer, the term of this patent is extended or adjusted under 35 U.S.C. 154(b) by 49 days.

(21) Appl. No.: 15/801,450

(22) Filed: Nov. 2, 2017

(65) Prior Publication Data

US 2018/0168669 A1 Jun. 21, 2018

Related U.S. Application Data

(60) Provisional application No. 62/435,136, filed on Dec. 16, 2016.

(51) Int. Cl.
| | | |
|---|---|---|
| *A61B 17/225* | (2006.01) | |
| *A61B 18/26* | (2006.01) | |
| *A61B 17/22* | (2006.01) | |
| *A61B 18/22* | (2006.01) | |
| *A61B 18/00* | (2006.01) | |
| *A61B 18/20* | (2006.01) | |

(52) U.S. Cl.
CPC ............ *A61B 17/225* (2013.01); *A61B 18/26* (2013.01); *A61B 2017/22024* (2013.01); *A61B 2017/22025* (2013.01); *A61B 2018/00505* (2013.01); *A61B 2018/00577* (2013.01); *A61B 2018/00982* (2013.01); *A61B 2018/20357* (2017.05); *A61B 2018/2238* (2013.01)

(58) Field of Classification Search
None
See application file for complete search history.

(56) References Cited

U.S. PATENT DOCUMENTS

| | | | | |
|---|---|---|---|---|
| 5,325,845 | A * | 7/1994 | Adair | A61B 1/0055 600/114 |
| 6,156,030 | A * | 12/2000 | Neev | A61B 18/20 606/10 |
| 9,549,666 | B2 * | 1/2017 | Hebert | A61B 1/0057 |
| 9,907,616 | B1 * | 3/2018 | Fried | A61B 18/26 |
| 2014/0005647 | A1 | 1/2014 | Shuffler et al. | |
| 2015/0100048 | A1 | 4/2015 | Hiereth et al. | |
| 2015/0230864 | A1 | 8/2015 | Xuan et al. | |
| 2015/0272674 | A1 | 10/2015 | Xuan et al. | |
| 2015/0313672 | A1 | 11/2015 | Milner et al. | |

* cited by examiner

*Primary Examiner* — Michael W Kahelin
*Assistant Examiner* — Elizabeth K So
(74) *Attorney, Agent, or Firm* — Schwegman Lundberg & Woessner, P.A.

(57) ABSTRACT

A surgical laser system comprises a laser source configured to generate laser energy; a laser fiber optically coupled to the laser source and configured to discharge the laser energy generated by the laser source; a rocker arm configured to control an orientation of the discharged laser energy; and a controller configured to control a movement of the rocker arm in response to feedback of the discharged laser energy or to pre-defined settings of the laser source.

15 Claims, 4 Drawing Sheets

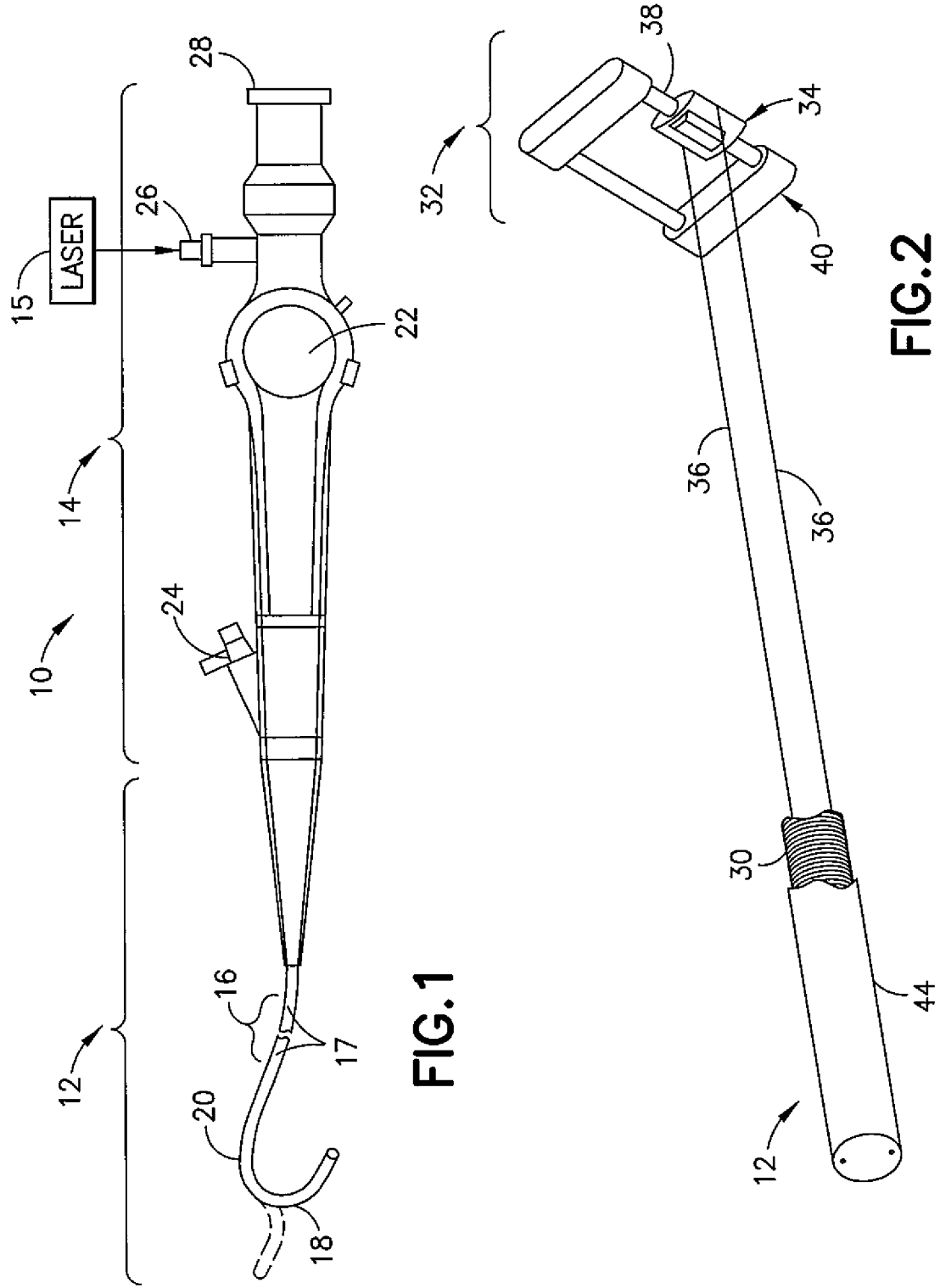

SCANNING URETEROSCOPE FOR MAXIMIZING EFFICIENCY IN LASER LITHOTRIPSY

CROSS REFERENCE TO RELATED APPLICATION

This application claims priority under 35 USC 119(e) to U.S. provisional patent application No. 62/435,136, filed Dec. 16, 2016, which is hereby incorporated by reference in its entirety.

BACKGROUND

Field of the Invention

The exemplary and non-limiting embodiments described herein relate to medical devices. More specifically, the exemplary and non-limiting embodiments described herein relate to surgical devices and mechanisms for the control of lasers in lithotripsy applications.

Brief Description of Prior Developments

U.S. Patent Publication No. 2014/0005647 describes a device having a catheter section comprising a flexible joint region disposed between distal and proximal ends with steerable and controllable medical laser fibers in the catheter section. U.S. Patent Publication No. 2015/0313672 describes providing sets of ideal values for laser parameters for the fragmentation and removal of calculi.

SUMMARY

In accordance with one aspect of the invention, a surgical laser system comprises a laser source configured to generate laser energy; a laser fiber optically coupled to the laser source and configured to discharge the laser energy generated by the laser source; a rocker arm configured to control an orientation of the discharged laser energy; and a controller configured to control a movement of the rocker arm in response to feedback of the discharged laser energy or to pre-defined settings of the laser source.

In accordance with another aspect of the invention, a surgical laser system for intracorporeal lithotripsy comprises an endoscope comprising a working channel, a proximal end, and a distal end configured to be deflectable; a laser source configured to generate laser energy; a laser fiber configured to be receivable within the working channel of the endoscope, and optically coupled to the laser source and configured to discharge the laser energy generated by the laser source; a rocker arm configured to be coupled with the proximal end of the endoscope to move the distal end of the endoscope; and a controller configured to control a movement, of the rocker arm in response to feedback of the discharged laser energy or to pre-defined settings of the laser source.

In accordance with another aspect of the invention, a method of ablating a stone using intracorporeal lithotripsy comprises emitting a first pulse of laser energy from a laser source and through a laser fiber and directing the first pulse at a stone; deflecting the laser fiber using a rocker arm; and emitting a second pulse of laser energy from the laser source and through the laser fiber and directing the second pulse at the stone.

BRIEF DESCRIPTION OF THE DRAWINGS

The foregoing aspects and other features of the invention are explained in the following description, taken in connection with the accompanying drawings, wherein:

FIG. 1 is a side view of one exemplary embodiment of an apparatus for use in a laser lithotripsy application;

FIG. 2 is a perspective view of one exemplary embodiment of a mechanism for controlling movement of a laser fiber of the apparatus of FIG. 1;

DETAILED DESCRIPTION

Figure 3:
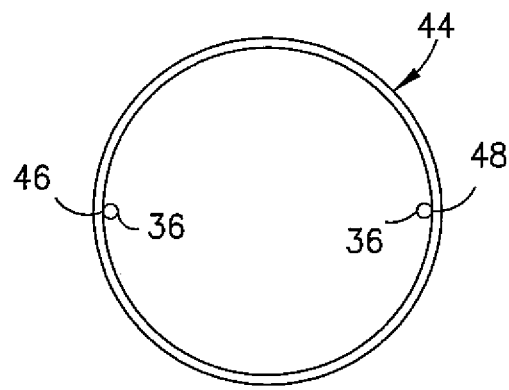
FIG. 3 is cross sectional view of a sheath at least partially encapsulating the laser fiber of FIG. 2.

Referring to FIG. 1, one exemplary embodiment of an apparatus or medical device is designated generally by the reference number 10 and is hereinafter referred to as "apparatus 10." Although the features will be described with reference to the example embodiments shown in the drawings, it should be understood that features can be embodied in many alternate forms. In addition, any suitable size, shape, or type of elements or materials could be used.

Apparatus 10 may be adapted to be used for intracorporeal laser lithotripsy. In intracorporeal laser lithotripsy, laser energy as a laser beam is directed onto a stone (calculus) in a patient's urinary tract to ablate the stone. A scanning speed of the laser beam is synchronized with a pulse rate of the laser beam to cause the stone to weaken and break apart. After breaking apart, the stone fragments may be removed using any suitable irrigation method.

The apparatus 10 has a front end 12 and a handle end 14 and is, in this embodiment, an endoscope (ureteroscope, cystoscope, renoscope, nephroscope, or the like) coupled with a laser 15. The laser 15 may be a holmium laser (e.g., Holmium:YAG (Ho:YAG)), a thulium laser (e.g., a Thulium Fiber Laser (TFL)), or any other laser that is suitable for the treatment or ablation of stones. One or more auxiliary devices (e.g., lights, ocular devices such as cameras or other imaging devices, irrigation devices, or the like) may also be included in the apparatus 10. A portion of the front end 12 may comprise a flexible shaft 16 having a working channel 17 defined therein, the flexible shaft 16 being configured to be partially inserted into a patient's body, such as through the patient's urethra, into the bladder, and possibly into the ureter to a point at which the stone is lodged. The flexible shaft 16 may comprise any suitable type of flexible shaft (e.g., plastic) and includes an active deflection section deflectable between a first position 18 and a second position 20. Deflection of the active deflection section to the first position 18 and the second position 20 may be carried out by manipulation of a user control 22 on the handle 14. A laser fiber (e.g., a quartz fiber or other fiber configured to facilitate optic transmission, shown at 30 in FIG. 2) coupled to the laser 15 may be carried through the working channel 17 of the flexible shaft 16. In addition to the user control 22, the handle 14 may include one or more ports 24 through which the auxiliary devices may be inserted, a port 26 for the laser 15 or other light source, and a port 28 for a suitable ocular device.

Referring to FIG. 2, deflection of the front end 12 of the apparatus 10 may be carried out mechanically in order to direct the laser energy emitted from the laser fiber 30. In one embodiment, the mechanization may be by cyclical deflection of the front end 12 (and a forward end of the laser fiber 30 accordingly) using a rocker arm assembly 32 associated with the user control 22 to cause a cyclical sweep of the laser fiber 30. The rocker arm assembly 32 comprises a rocker arm 34 configured to act on deflection cables 36. The rocker arm 34 may be rotatable about an axis 38 supported in a cradle 40 or other suitable structure. Proximal ends of the deflection cables 36 may be coupled to the rocker arm 34 at opposing sides thereof and on opposite sides of the axis 38. Distal ends of the deflection cables 36 may be coupled to the front end 12 proximate the tip of the laser fiber 30. In one exemplary embodiment, the laser fiber 30 is carried through a sheath 44 in the working channel 17, with the distal ends of the deflection cables 36 attached to the sheath 44.

Referring to FIG. 3, the distal ends of the deflection cables 36 may be attached to the sheath 44 at opposite points 46, 48 on the inner circumference (or outer circumference) of a cross section of the sheath 44. In such a configuration and when the front end 12 is not deflected, the rocker arm 34 is in a neutral position, and both deflection cables 36 are substantially equally tensioned. The axle 38 may be spring-loaded to return to the neutral position when no deflection of the front end 12 is desired.

Upon rotation of the axle 38 to cause the rocker arm 34 to rock about the axle 38, one of the deflection cables 36 is pulled and the other one is relaxed. Because the distal ends of the deflection cables 36 are attached to the sheath 44 at opposite points 46, 48, the deflection of the front end 12 is along a 180 degree line perpendicular to the direction in which the sheath 44 extends. Additionally, a force used to deflect the front end 12 a given distance in one direction is substantially equal to a force, used to deflect the front end 12 the same distance in an opposing direction. Repeated rocking of the rocker arm 34 causes the cyclical deflection of the front end 12. The laser 15 may be configured to emit a pulse of laser energy based on a position of the rocked rocker arm 34.

In one embodiment, the cyclical deflection of the rocker arm 34 may be controlled manually by the surgeon. In carrying out the deflection manually, the axle 38 may be rotatable in the cradle 40 through a system of gears (e.g., planetary gears) arranged such that a relatively large movement in the surgeon's hand causes a very small movement of the axle 38 and the rocker arm 34 (and corresponding small movements of the deflection cables 36 and the front end 12), thus allowing for precise control in the orientation of the laser fiber 30 relative to the targeted stone.

However, in general, because relying on a surgeon to control the synchronization of the scanning speed of the laser beam with the pulse rate of the laser beam by finger movement is not generally practical or feasible, the movement of the front end 12 of the apparatus 10 may be controlled via a computer. In such an embodiment, the cyclical deflection of the rocker arm 34 may be carried out by rotation of the axle 38 through commands input to the computer and relayed to a motor. The axle 38 may be directly coupled to a rotor of the motor, or it may be coupled to the rotor through a system of gears. When the rotor spins, the deflection cables 36 are pulled to deflect the front end 12. If a system of gears is incorporated into the motor, then several rotations of the rotor may cause a very small movement of the deflection cables 36, thus allowing for precise control. In doing so, the front end 12 deflects cyclically to execute a scan motion with controlled speed and period. The controlled speed and period of the scan motion may be coordinated with the laser 15 to provide a pulse of energy from the laser 15 when the rocker arm 34 is rocked completely away from the neutral position in each direction.

In inputting commands to the motor, the commands may be input using any suitable input device associated with the computer system. In particular, the commands may be input using keys on a keyboard or using a pointing device such as a mouse, stylus, stylus/touchscreen combination, or the like.

Figure 4:
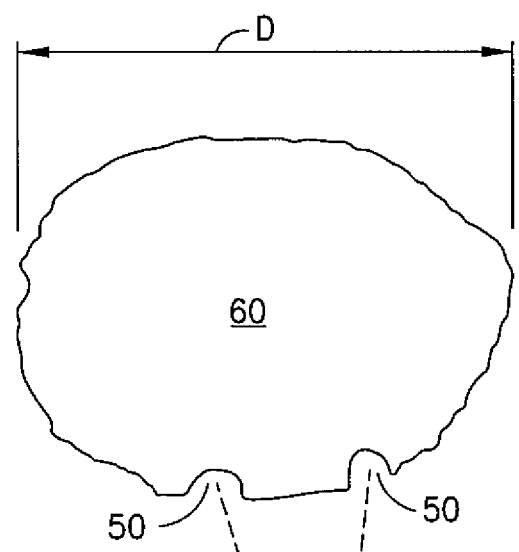
FIG. 4 is a schematic representation of one exemplary embodiment of a use of a laser in a laser lithotripsy method.

Referring to FIG. 4, a laser lithotripsy method employing a "dusting" technique may be carried out by the surgeon in order to manipulate the laser fiber 30 through a ureteroscope to apply pulsed laser energy to the surface of the stone to break the stone into smaller pieces, which may be removed from the patient by suction or irrigation or which may be carried out of the patient naturally by urination. In carrying out a typical dusting technique, the laser energy is directed onto the stone to form a cavity, which, upon removal of stone material, fills with water, irrigation fluid such as saline, or other material. Higher amounts of laser energy and increased frequency of pulses may ablate a stone faster, but in a typical dusting technique the laser energy passes through the water, irrigation fluid, or other material that fills the cavity as the cavity forms. The water, irrigation fluid, or other material filling the cavity becomes heated (possibly to a temperature that may cause discomfort to the patient). In doing so, only a small proportion of subsequent pulses of the laser energy hits the stone surface, with a larger proportion of the laser energy being absorbed by the water, irrigation fluid, or other material filling the cavity.

In the embodiments employing the apparatus 10 described herein, the rocker arm 34 may be cyclically deflected via the controls such that reasonable amounts of laser energy can be selectively applied to areas of the stone to ablate the stone while minimizing any undesirable heating effects in the patient. For example, the apparatus 10 may be controlled, during a surgical procedure, with efficient energy utilization to direct the laser energy from the laser pulses onto the stone while minimizing the amount of laser energy that is absorbed by the water, irrigation fluid, or other material such that heating effects to the patient are minimized.

For example, the energy pulse from the laser 15 through the laser fiber 30 may be configured to create craters 50 of limited depth in a stone 60 having a diameter D. In the embodiments employing the apparatus 10 described herein, cyclical movement of the rocker arm 34 may be coordinated with the laser pulse such that laser energy from each consecutive pulse is applied to two areas of the stone 60 (rather than into one area in which a hole is continuously bored, thus filling with an increasing amount of fluid), which means that more laser energy is spent on breaking the stone 60 rather than heating the water, irrigation fluid, or other material.

Figure 5:
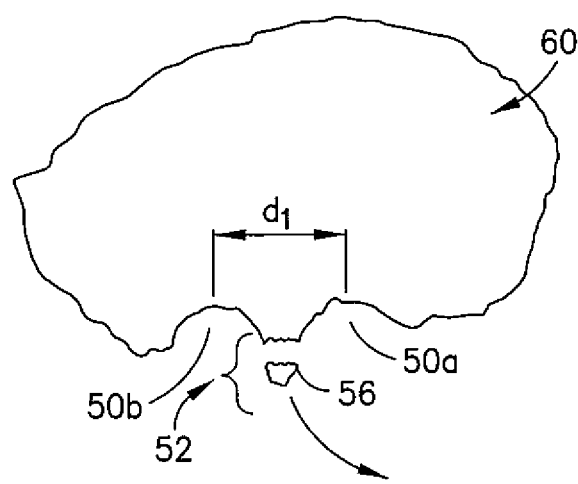
FIG. 5 is a schematic representation of a stone fragmented by the method of FIG. 4.

Referring to FIG. 5, the rocker arm 34 may be controlled such that subsequent energy pulses may strike the stone 60 at distance $d_1$ away from a first crater 50a to form a second crater 50b having a ridge 52 between the first crater 50a and the second crater 50b. Depending upon the distance $d_1$, the ridge 52 may be sufficiently thin and weak, thereby creating frangible portions 56 at the outer surface of the stone 60 that break off from the mass of the stone 60 as by-products of the close proximity of consecutively created craters. Thus, improved efficiency is realized, and the mass reduction rate of lithotripsy (how fast the stone 60 is removed) carried out using the apparatus 10 is increased.

Figure 6:
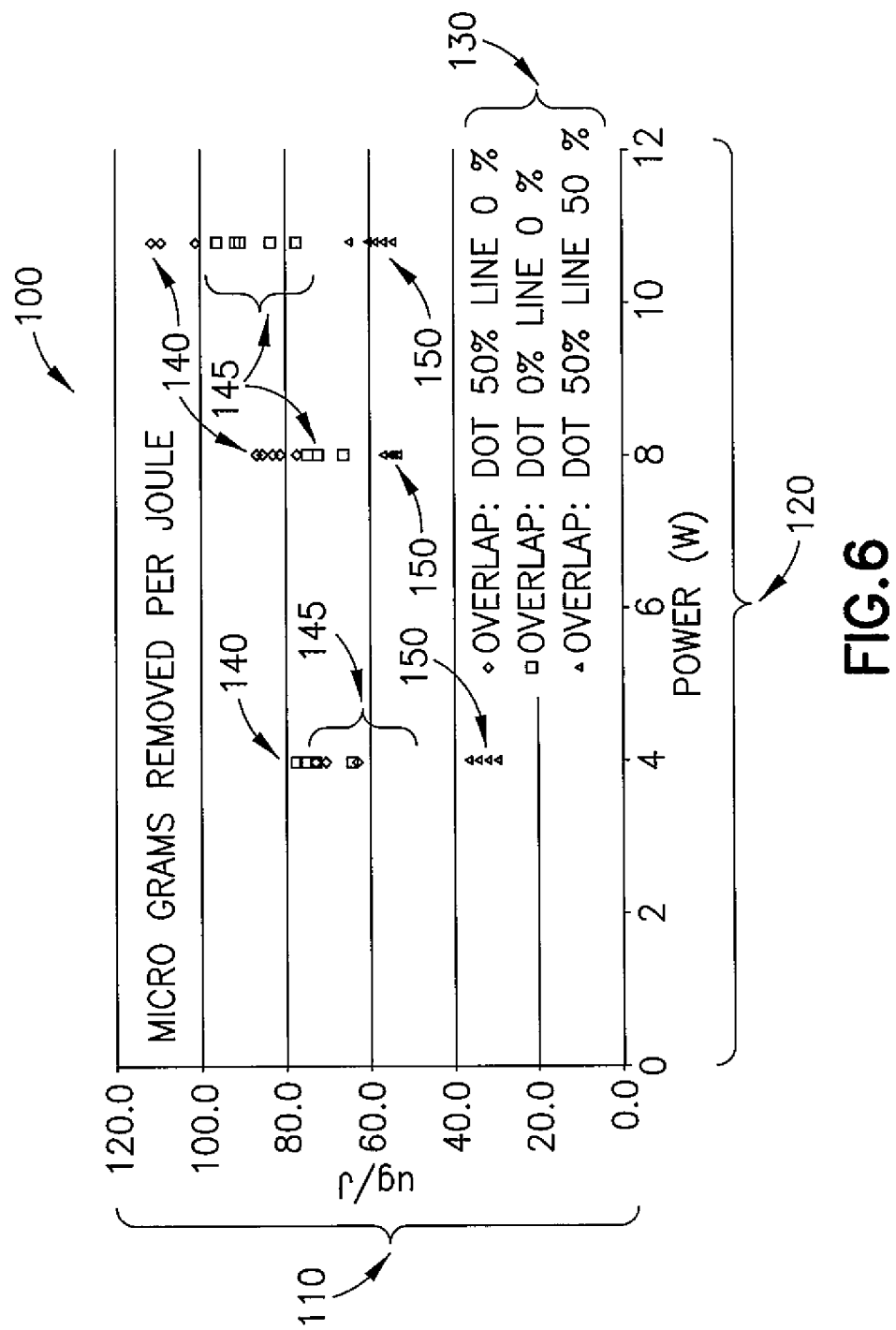
FIG. 6 is a graphical representation of the efficiency of a laser lithotripsy method using the apparatus of FIG. 1.

Referring to FIG. 6, the energy efficiency of laser lithotripsy using the apparatus 10 is shown graphically at 100. In the graph 100, the mass of a stone removed per unit energy (watts (W)) is shown at 110 versus average power of a laser shown at 120. As shown, by moving the laser beam at a speed proportional to the laser pulsing rate, the ablation efficiency, in terms of how much stone mass (e.g., in micrograms (ug)) can be removed by each unit of energy (e.g., in joules (J)) released to the stone, can be higher or lower.

In the graph 100, the diameter of the laser fiber 30 produces a "dot" or area on the stone from which material may be removed. A series of "dots" may extend horizontally across a surface of the stone. The movement of the laser 15 horizontally is generally mechanical; however, optimal control of the movement is generally carried out using a computer.

In correspondence with a legend 130 of the graph 100, a 50% overlap of each dot with no overlap of horizontal lines produces higher removal rates at any average power, a 0% overlap of each dot with a 50% overlap of horizontal lines produces a lower removal rate at any average power, and a 50% overlap of each dot with a 50% overlap of horizontal lines produces the lowest removal rate at any average power. The highest removal rates are shown at 140, with intermediate removal rates being shown at 145, and the lowest removal rates being shown at 150. The average power 120 of the laser may be defined by the product of any number of J per pulse and number of pulses. For example, an average power 120 at 4 W may be (0.5 J/pulse*8 pulses) or (1 J/pulse*4 pulses), etc. At any average power level (4, 8, or 11 W), increasing the energy increases the rate of removal of the stone.

Figure 7:
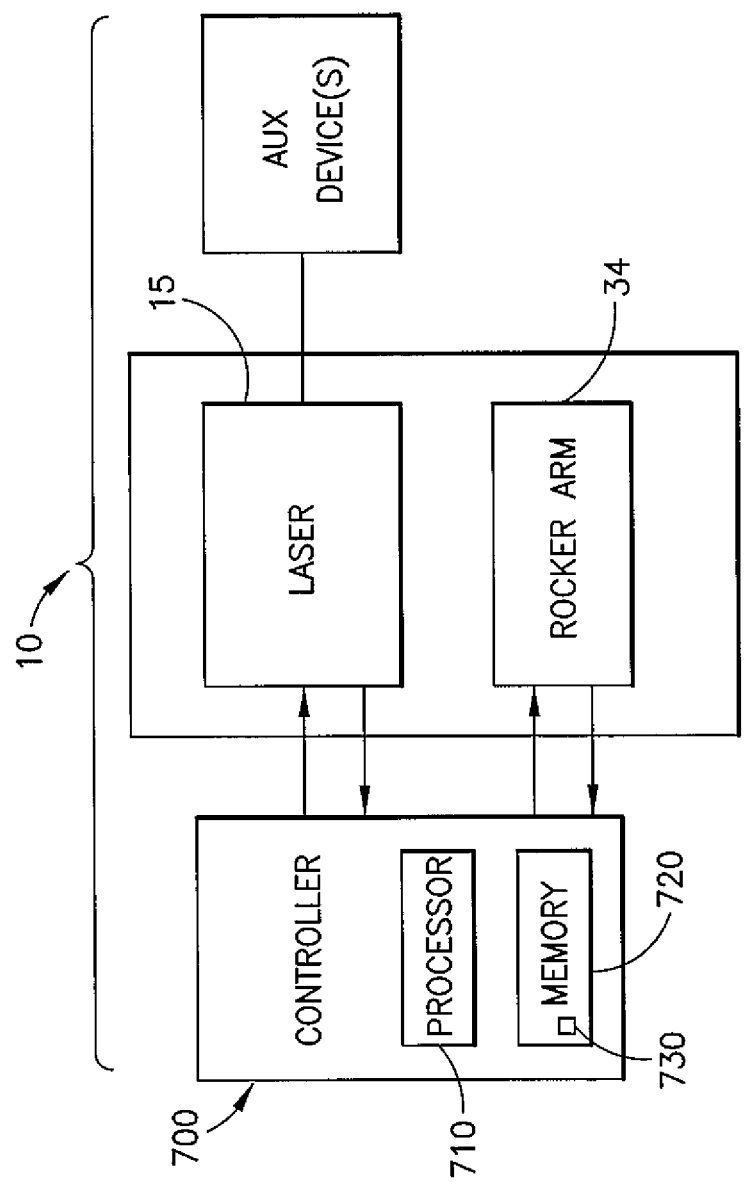
FIG. 7 is a block diagram illustrating control of the apparatus of FIG. 1.

Referring to FIG. 7, the apparatus 10, particularly the laser portion thereof, may be controlled by a controller 700 having a processor 710, a memory 720, and software 730. The controller 700 may be configured to coordinate the cyclical deflection of the rocker arm 34 with a pulse rate of the laser 15 to allow the surgeon to carry out a dusting technique. In one exemplary embodiment, for example, feedback of the discharged laser energy can be returned to the controller 700, or the controller 700 can operate based on pre-defined settings of the laser fiber 30 (e.g. power settings, frequency settings, and the like).

In any embodiment, the surgeon may determine the position of a stone relative to the apparatus inserted into the patient through observation (e.g., through a camera or the like incorporated into the apparatus 10 as the auxiliary device). An image of the stone may be displayed on a screen. Once the position of the stone is determined, the surgeon may define areas (for example, by selecting areas on the display using a mouse or other pointing device) indicating where the laser energy is to be applied. Once a desired amount of the stone has been bombarded with laser energy and cavities formed (or ablation occurs), the apparatus 10 may be repositioned and the dusting technique may be continued until the stone is sufficiently ablated.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced, or utilized in any combination (e.g., any combination that is suitable, practicable and/or feasible) and are not limited only to those combinations described herein and/or included in the appended claims.

In one exemplary embodiment, a surgical laser system comprises a laser source configured to generate laser energy; a laser fiber optically coupled to the laser source and configured to discharge the laser energy generated by the laser source; a rocker arm configured to control an orientation of the discharged laser energy; and a controller configured to control a movement of the rocker arm in response to feedback of the discharged laser energy or to pre-defined settings of the laser source.

The rocker arm may be coupled to a forward end of the laser fiber via at least two cables such that movement of the rocker arm causes movement of at least one of the cables to cause deflection of the forward end of the laser fiber. The laser fiber may be at least partially encased in a sheath, and movement of the rocker arm may cause deflection of the forward end of the laser fiber by pulling on the sheath. The rocker arm may be configured to rock about an axis extending through the rocker arm. The controller may comprise at least a processor and a memory and may be configured to coordinate a cyclic deflection of the rocker arm with a pulse rate of the laser source. The laser source may be a holmium laser or a thulium laser.

In another exemplary embodiment, a surgical laser system for intracorporeal lithotripsy comprises an endoscope comprising a working channel, a proximal end, and a distal end configured to be deflectable; a laser source configured to generate laser energy; a laser fiber configured to be receivable within the working channel of the endoscope, and optically coupled to the laser source and configured to discharge the laser energy generated by the laser source; a rocker arm configured to be coupled with the proximal end of the endoscope to move the distal end of the endoscope; and a controller configured to control a movement of the rocker arm in response to feedback of the discharged laser energy or to pre-defined settings of the laser source.

The system may further comprise at least two cables coupling opposing ends of the rocker arm to the laser fiber at the distal end of the endoscope. The laser fiber may be at least partially encapsulated in a sheath carried through the working channel, and distal ends of the at least two cables may be coupled to the sheath proximate a distal end of the laser fiber. The rocker arm may be positioned on an axle, the axle being rotatable to move the rocker arm. The control of the rocker arm by the controller may comprise a coordination of a cyclic deflection of the rocker arm with a pulse rate of the laser source. The pre-defined settings of the laser source may comprise power and frequency settings. The laser source may be a Holmium:YAG laser or a Thulium Fiber Laser. The system may further comprise at least one auxiliary device operably coupled to the endoscope.

In another exemplary embodiment, a method of ablating a stone using intracorporeal lithotripsy comprises emitting a first pulse of laser energy from a laser source and through a laser fiber and directing the first pulse at a stone; deflecting the laser fiber using a rocker arm; and emitting a second pulse of laser energy from the laser source and through the laser fiber and directing the second pulse at the stone.

In the method, deflecting the laser fiber using a rocker arm may comprise cyclically deflecting the rocker arm to cause a cyclical sweep of the laser fiber from which the laser energy is emitted. The method may further comprise controlling the deflecting of the laser fiber using a rocker arm in response to feedback of discharged laser energy or to pre-defined settings of the laser source.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A surgical laser system, comprising:
   a laser source configured to generate laser energy;
   a laser fiber optically coupled to the laser source and configured to discharge the laser energy generated by the laser source;
   a rocker arm configured to control an orientation of the discharged laser energy between a first position and a second position; and
   a controller configured to control a movement of the rocker arm from the first position, through a neutral position, and to the second position in response to feedback of a pulse rate of the discharged laser energy or to pre-defined pulse rate settings of the laser source;
   wherein the discharged laser energy from the laser fiber is based on the first position and the second position of the rocker arm; and
   wherein in the neutral position the laser energy is not discharged.

2. The surgical laser system of claim 1, wherein the rocker arm is coupled to a forward end of the laser fiber via at least two cables such that movement of the rocker arm causes movement of at least one of the cables to cause deflection of the forward end of the laser fiber.

3. The surgical laser system of claim 2, wherein the laser fiber is at least partially encased in a sheath, and wherein movement of the rocker arm causes deflection of the forward end of the laser fiber by pulling on the sheath.

4. The surgical laser system of claim 1, wherein the rocker arm is configured to rock about an axis extending through the rocker arm.

5. The surgical laser system of claim 1, wherein the controller comprises at least a processor and a memory and is configured to coordinate a cyclic deflection of the rocker arm with the pulse rate of the laser source.

6. The surgical laser system of claim 1, wherein the laser source is a holmium laser or a thulium laser.

7. A surgical laser system for intracorporeal lithotripsy, the system comprising:
   an endoscope comprising a working channel, a proximal end, and a distal end configured to be deflectable;
   a laser source configured to generate laser energy;
   a laser fiber configured to be receivable within the working channel of the endoscope, and optically coupled to the laser source and configured to discharge the laser energy generated by the laser source;
   a rocker arm configured to be coupled with the proximal end of the endoscope to move the distal end of the endoscope; and
   a controller configured to control a movement of the rocker arm from a first position, through a neutral position, and to a second position in response to feedback of a pulse rate of the discharged laser energy or to pre-defined pulse rate settings of the laser source;
   wherein the discharged laser energy from the laser fiber is based on the first position and the second position of the rocker arm; and
   wherein in the neutral position the laser energy is not discharged.

8. The surgical laser system of claim 7, further comprising at least two cables coupling opposing ends of the rocker arm to the laser fiber at the distal end of the endoscope.

9. The surgical laser system of claim 8, wherein the laser fiber is at least partially encapsulated in a sheath carried through the working channel and wherein distal ends of the at least two cables are coupled to the sheath proximate a distal end of the laser fiber.

10. The surgical laser system of claim 7, wherein the rocker arm is positioned on an axle, the axle being rotatable to move the rocker arm.

11. The surgical laser system of claim 7, wherein the control of the rocker arm by the controller comprises a coordination of a cyclic deflection of the rocker arm with the pulse rate of the laser source.

12. The surgical laser system of claim 7, wherein the pre-defined settings of the laser source comprise power and frequency settings.

13. The surgical laser system of claim 7, wherein the laser source is a Holmium:YAG laser.

14. The surgical laser system of claim 7, wherein the laser source is a Thulium Fiber Laser.

15. The surgical laser system of claim 7, further comprising at least one auxiliary device operably coupled to the endoscope.

* * * * *